United States Patent [19]

Yamabe et al.

[11] 4,151,200
[45] Apr. 24, 1979

[54] PROCESS FOR PRODUCING POLYFLUORODIACYL FLUORIDE

[75] Inventors: Masaaki Yamabe, Machida; Seisaku Kumai, Yokohama, both of Japan

[73] Assignee: Asahi Glass Company Ltd., Tokyo, Japan

[21] Appl. No.: 844,917

[22] Filed: Oct. 25, 1977

[51] Int. Cl.$^2$ .................................... C07C 51/58
[52] U.S. Cl. .................................... 260/544 F
[58] Field of Search .................................... 260/544 F

[56] References Cited

U.S. PATENT DOCUMENTS

| | | | |
|---|---|---|---|
| 3,250,806 | 5/1966 | Warnell | 260/544 F |
| 3,274,239 | 9/1966 | Selman | 260/544 F |
| 4,035,388 | 7/1977 | Martini | 260/544 F |

Primary Examiner—Gerald A. Schwartz
Attorney, Agent, or Firm—Oblon, Fisher, Spivak, McClelland & Maier

[57] ABSTRACT

Polyfluorodiacyl fluorides having the formula $$FOC(CFXOCF_2)_p(CF_2)_{n-1}(CF_2OCFX)_qCOF$$

wherein n represents an integer of 2 to 4; X represents fluorine or chlorine atom or trifluoromethyl group; p=0 to 5; q=0 to 5; p+q>1 are produced by reacting a perfluorolactone with a fluorocarbon epoxide, optionally in the presence of an aprotic polar solvent and a nucleophilic reagent.

8 Claims, No Drawings

PROCESS FOR PRODUCING POLYFLUORODIACYL FLUORIDE

BACKGROUND OF THE INVENTION

1. Field of the Invention

The present invention relates to a process for producing a polyfluorodiacyl fluoride. More particularly, it relates to a novel process for producing a polyfluorodiacyl fluoride by reacting a perfluorolactone with a fluorocarbon epoxide.

2. Description of the Prior Art

The polyfluorodiacyl fluorides obtained by the process of the present invention are useful as intermediates for various reactions. For example, the polyfluorodiacyl fluorides can be easily converted to the corresponding polyfluoroether dicarboxylic acids by hydrolysis. The resulting dicarboxylic acids can be used as starting materials for producing fluorinated polyesters and fluorinated polyamides. The polyfluorodiacyl fluoride obtained by using hexafluoropropylene oxide.

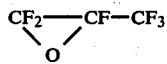

as the fluorocarbon epoxide can be easily converted to the corresponding perfluorodivinyl ether by the pyrolysis under suitable condition as disclosed in Japanese Patent Publication No. 1617/1963.

SUMMARY OF THE INVENTION

It is an object of the present invention to provide a process for producing polyfluorodiacyl fluorides as useful intermediates in various reactions.

It is another object of the present invention to provide a process for producing polyfluorodiacyl fluorides by reacting a specific perfluorolactone with a fluorocarbon epoxide in high yield through a less complicated process.

The foregoing and other objects of the present invention have been attained by producing a polyfluorodiacyl fluoride having the formula $$FOC(CFXOCF_2)_p(CF_2)_{n-1}(CF_2OCFX)_qCOF$$

wherein n and X are defined below and p represents 0 to 5 and q represents 0 to 5 and p+q is more than 1, by reacting a perfluorolactone having the formula

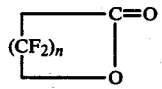

wherein n represents an integer of 2 to 4 with a fluorocarbon epoxide having the formula

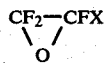

wherein X represents fluorine or chlorine atom or trifluoromethyl group.

DETAILED DESCRIPTION OF THE PREFERRED EMBODIMENTS:

The perfluorolactones used in the process of the present invention can be obtained by heating silver perfluoroglutarate in the presence of iodine as disclosed in J.A.C.S. 74, 1974(1952), etc. The perfluorolactones can be also easily obtained by treating perfluorodiiodide having the formula $I(CF_2)_{3-5}I$ with fuming sulfuric acid.

On the other hand, the fluorocarbon epoxides can be easily obtained by reacting a fluorinated olefin with oxygen or a peroxide as disclosed in Japanese Patent Publication Nos. 4753/1962, 20108/1963 and 11683/1970.

The reaction conditions in the process of the present invention are not critical, however, in order to smoothly perform the reaction, it is preferable to use suitable solvents such as aliphatic polyethers having carbon atoms of 4 to 16; hydrocarbon nitriles having carbon atoms of 2 to 12, etc.

Suitable solvents include ethyleneglycol dimethyl ether, diethyleneglycol dimethyl ether, dioxane, acetonitrile, propionitrile, etc. It is also possible to use, as the solvent, dimethylformamide, dimethylsulfoxide, N-methylpyrrolidone, nitroethane, tetrahydrofuran, etc. The aprotic polar solvents are preferably used. It is optimum to use ethyleneglycol dimethyl ether.

In order to perform the reaction in high reaction rate, it is preferable to react them in the presence of a nucleophilic reagent.

Suitable nucleophilic reagents include potassium fluoride, cesium fluoride, silver fluoride, quaternary ammonium fluoride, etc. It is optimum to use cesium fluoride.

The amount of the nucleophilic reagent is not critical and is usually about 0.1 to 100 mole % preferably about 1 to 20 mole % based on the perfluorolactone.

It is also possible to use a solvent such as fluorochlorohydrocarbon e.g. trichlorotrifluoroethane, tetrachlorodifluoroethane; and chlorinated hydrocarbons e.g. methylenechloride, chloroform, dichloroethane, trichloroethane, tetrachloropropane, etc.

The reaction temperature can be in a range of about $-80°$ C. to $+200°$ C. preferably about $-30°$ C. to $+50°$ C. which is not critical.

The reaction pressure can be spontaneous pressure and can be also higher pressure, if necessary.

The mole ratio of the perfluorolactone to the fluorocarbon epoxide is selected depending upon the structure of the object polyfluorodiacyl fluoride having the formula $$FOC(CFXOCF_2)_p(CF_2)_{n-1}(CF_2OCFX)_qCOF$$

and the values of p and q and the kinds of the starting materials.

In general, it is preferable to use the fluorocarbon epoxide in slightly excess to the stoichiometric moles of the epoxide for forming the object structure. For example, in order to obtain the polyfluorodiacyl fluoride having the formula wherein n=3; p—1; q—0 and X=trifluoromethyl group as the object product in high yield, it is preferable to use about 1 to 1.3 mole of hexafluoropropylene oxide per 1 mole of perfluoro-γ-butyrolactone

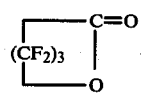

Thus, it is possible to obtain the object product of polyfluorodiacyl fluoride

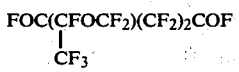

in high yield of more than about 80%. The perfluoro-2,9-dimethyl-3,8-dioxadecanedioyl fluoride

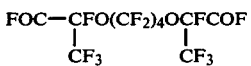

can be obtained in high yield of more than 80% by using about 2.2 to 2.4 moles of hexafluoropropylene oxide per 1 mole of perfluoro-γ-butyrolactone.

The invention will be further illustrated by certain specific examples which are included for purposes of illustration only and not intended to be limiting unless otherwise specified.

EXAMPLE 1:

Preparation of perfluoro-2-methyl-3-oxaheptanedioyl fluoride:

In a 300 cc autoclave equipped with a mechanical stirrer, 15 g of cesium fluoride powder was charged and it was dried and it was kept in a pressure of about 1 mmHg and 50 cc of ethyleneglycol dimethyl ether was charged. The autoclave and the components in the autoclave were cooled to −35° C. in a dry-ice bath and 135 g (0.696 mole) of perfluoro-γ-butyrolactone and 128 g (0.771 mole) of hexafluoropropylene oxide were charged in the autoclave to condensate them. The autoclave was heated to the room temperature for 3 hours with vigorously stirring them under maintaining the pressure of lower than 1.5 kg/cm$^2$.

The fluorocarbon layer was separated and distilled to obtain 220 g (yield 87.8 mole %) of perfluoro-2-methyl-3-oxaheptanedioyl fluoride. (bp. 86° C.).

EXAMPLE 2:

Preparation of perfluoro-2-methyl-3-oxaheptanedioyl fluoride:

In a 1 liter autoclave equipped with a mechanical stirrer, 51 g of cesium fluoride powder was charged and dried and it was kept in a pressure of about 1 mmHg, and 250 cc of ethyleneglycol dimethyl ether and 421 g (2.17 mole) of perfluoro-γ-butyrolactone were charged, and then, 424 g (2.55 mole) of hexafluoropropylene oxide was intermittently added for 2.5 hours with vigorously stirring at the reaction temperature of 0° to 10° C. under a pressure of lower than 2 kg/cm$^2$.

After the reaction, the fluorocarbon layer was separated and distilled to obtain 585.5 g (yield 74.9 mole %) of perfluoro-2-methyl-3-oxaheptanedioyl fluoride. (bp. 86° C.).

EXAMPLE 3:

Preparation of perfluoro-2,9-dimethyl-3,8-dioxadecanedioyl fluoride:

In a 500 cc autoclave equipped with a mechanical stirrer, 15 g of cesium fluoride powder was charged and dried and it was kept in a pressure of about 1 mmHg and 45 cc of ethyleneglycol dimethyl ether and 135 g (0.696 mole) of perfluoro-γ-butyrolactone were charged and then, 272 g (1.64 mole) of hexafluoropropylene oxide was intermittently added for about 2.0 hours with vigorously stirring at the reaction temperature of 0° to 10° C. under a pressure of lower than 1.5 kg/cm$^2$.

After the reaction, the fluorocarbon layer was separated and distilled to obtain

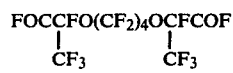

(b.p. 89° to 92° C./50 mmHg). The yield was 82% based on perfluoro-γ-butyrolactone.

EXAMPLE 4:

Preparation of perfluoro-2-methyl-3-oxahexanedioyl fluoride:

In a 200 cc autoclave equipped with a mechanical stirrer, 7.5 g of cesium fluoride powder was charged and dried and it was kept in a pressure of about 1 mmHg and 15 cc of ethyleneglycol dimethyl ether was charged. The autoclave and the components in the autoclave were cooled to −35° C. in a dry-ice bath and 50 g (0.347 mole) of perfluoro-β-propiolactone and 63.4 g (0.389 mole) of hexafluoropropylene oxide were charged in the autoclave to condensate them. The autoclave was heated to the room temperature for 2.5 hours with vigorously stirring them under maintaining the pressure of lower than 1.5 kg/cm$^2$.

The fluorocarbon layer was separated and distilled to obtain 87.1 g (yield 81.0 mole %) of perfluoro-2-methyl-3-oxahexanedioyl fluoride having the formula

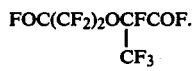

EXAMPLE 5:

Preparation of perfluoro-3-oxaheptanedioyl fluoride:

In a 200 cc autoclave equipped with a mechanical stirrer, 5.6 g of cesium fluoride powder was charged and dried and it was kept in a pressure of about 1 mmHg and 15 cc of ethyleneglycol dimethyl ether and 50.0 g (0.258 mole) of perfluoro-γ-butyrolactone were charged and then, 34.4 g (0.297 mole) of tetrafluoroethylene oxide was intermittently added for about 2.0 hours with vigorously stirring at the reaction temperature of 0° to 10° C. under a pressure of lower than 2.0 kg/cm$^2$.

After the reaction, the fluorocarbon layer was separated and distilled to obtain 64.0 g (yield 80.0 mole %) of perfluoro-3-oxaheptanedioyl fluoride.

EXAMPLE 6:

Preparation of perfluoro-2-methyl-3-oxaoctanedioyl fluoride:

In a 200 cc autoclave equipped with a mechanical stirrer, 5 g of cesium fluoride powder, 20 cc of ethyleneglycol dimethyl ether and 50 g of perfluoro-δ-valerolactone was charged. Thirty seven grams of hexafluoropropylene oxide was introduced intermittently into the reactor for about 2 hours with vigorously stirring at the temperature of 0° to 5° C. under a pressure of lower than 1.0 kg/cm$^2$G.

The fluorocarbon layer was separated from the reaction mixture and distilled to obtain

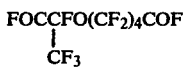

(bp. 102°–105° C./50 mmHg). The yield was 85% based on perfluoro-δ-valerolactone.

REFERENCE 1:

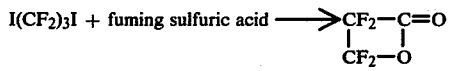

In an autoclave, were placed 1 kg of fuming sulfuric acid containing 30 wt.% of SO₃ and 200 g of 1,3-diiodoperfluoropropane, which was synthesized according to the method described in J.A.C.S., 74, 1974 (1952). The mixture was stirred at 100° C. for 10 hours. The gaseous reaction products were collected and carefully distilled. As the result, 18 g of perfluoro-β-propiolactone was obtained.

REFERENCE 2:

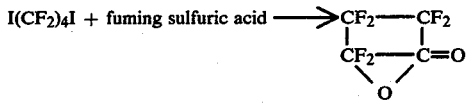

In a 25 liter glass reactor equipped with a thermometer, a reflux condenser, a dropping funnel and a stirrer, 41 kg of fuming sulfuric acid containing 30 wt.% of SO₃ was charged and heated at 90° C. and then 9.15 kg of 1,4-diiodoperfluorobutane was added dropwise during 8 hours. The reaction mixture was collected and separated by distillation. As the result, 1.6 kg of perfluoro-γ-butyrolactone was obtained.

REFERENCE 3:

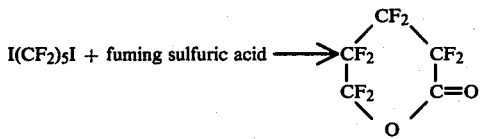

1,5-Diiodoperfluoropentane was obtained by the reaction of 1,3-diiodoperfluorobutane with tetrafluoroethylene in the presence of azobisisobutyronitrile at 80° C.

In an autoclave, were placed 2.1 kg of fuming sulfuric acid containing 30 wt.% of SO₃ and 504 g of 1,5-diiodoperfluoropentane. The mixture was heated at 120° C. for 13 hours under vigorously stirring. The fluorocarbon layer was separated from the reaction mixture and 53 g of perfluoro-δ-valerolactone was isolated by distillation.

What is claimed is:

1. A process for producing a polyfluorodiacyl fluoride having the formula

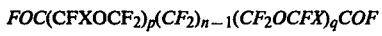

wherein n represents an integer of 2 to 4; X represents fluorine or chlorine atom or trifluoromethyl group; p represents 0 to 5; q represents 0 to 5; and p+q is more than 1, which comprises reacting a perfluorolactone having the formula:

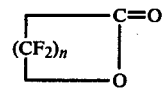

wherein n represents an integer of 2 to 4; with a fluorocarbon epoxide having the formula

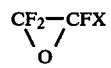

wherein X represents fluorine or chlorine atom or trifluoromethyl group; wherein the reaction is carried out under spontaneous pressure or higher at the reaction temperature of −80° C. to +200° C.

2. A process according to claim 1 wherein the reaction is carried out in a solvent.

3. A process according to claim 2 wherein the solvent is an aliphatic polyether having carbon atoms of 4 to 16 or a hydrocarbon nitrile having carbon atoms of 2 to 12 or other aprotic polar solvent.

4. A process according to claim 2, wherein the solvent is ethyleneglycol dimethyl ether, diethyleneglycol dimethyl ether, dioxane, acetonitrile, propionitrile, dimethylformamide, dimethylsulfoxide, N-methylpyrrolidone, nitroethane, or tetrahydrofuran.

5. A process according to claim 1 wherein the reaction is carried out in the presence of a nucleophilic reagent.

6. A process according to claim 5 wherein the nucleophilic reagent is potassium fluoride, cesium fluoride, silver fluoride, quaternary ammonium fluoride.

7. A process according to claim 1 wherein a mole ratio of the fluorocarbon epoxide to the perfluorolactone is higher than stoichiometrical value.

8. A process for producing a polyfluorodiacyl fluoride having the formula

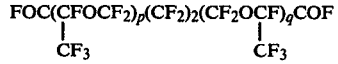

wherein p represents 0 to 5; q represents 0 to 5; and p+q is more than 1, which comprises reacting perfluoro-γ-butyrolactone with hexafluoropropylene oxide.

* * * * *